(12) United States Patent
Erhardt et al.

(10) Patent No.: US 7,709,216 B2
(45) Date of Patent: May 4, 2010

(54) METHODS FOR PREVENTING OR REDUCING ISCHEMIA/REPERFUSION INDUCED MYOCARDIAL CELL DEATH

(75) Inventors: Peter Erhardt, Natick, MA (US); Ambrus Toth, Chestnut Hill, MA (US)

(73) Assignee: Boston Biomedical Research Institute, Watertown, MA (US)

( * ) Notice: Subject to any disclaimer, the term of this patent is extended or adjusted under 35 U.S.C. 154(b) by 0 days.

(21) Appl. No.: 11/891,015

(22) Filed: Aug. 8, 2007

(65) Prior Publication Data

US 2008/0009030 A1    Jan. 10, 2008

Related U.S. Application Data

(62) Division of application No. 11/103,851, filed on Apr. 12, 2005, now abandoned.

(60) Provisional application No. 60/561,640, filed on Apr. 13, 2004.

(51) Int. Cl.
*A61K 39/395* (2006.01)

(52) U.S. Cl. .................. 435/7.1; 435/7.2; 436/501; 436/503

(58) Field of Classification Search ........... None
See application file for complete search history.

(56) References Cited

U.S. PATENT DOCUMENTS

2004/0214902 A1 * 10/2004 Wang et al.

OTHER PUBLICATIONS

Nakano et al. *Molecular Cell*, vol. 7, pp. 683-694, 2001.*
K. Nakano and K.H. Vousden, PUMA, a novel proapoptotic gene, is induced by p53. Molecular Cell, 7: 683-694 (Mar. 2001).
T. Hershko and D. Ginsberg, Up-regulation of bcl-2 homology 3 (BH3)-only proteins by E2F1 mediates apoptosis. J. of Biological Chem., 279(10): 8627-8634 (Mar. 2004).
J. Yu et al., PUMA induces the rapid apoptosis of colorectal cancer cells. Molecular Cell, 7: 673-682 (Mar. 2001).
K. Vousden, p53 and PUMA: A deadly duo. Science, 309: 1685-1686 (Sep. 2005).
J. Yu and L. Zhang, No PUMA, no death: Implications for p53-dependent apoptosis. Cancer Cell, pp. 248-249 (Oct. 2003).
Melino et al., J. of Biol. Chem. 279: 8076-8083 (2004).

* cited by examiner

*Primary Examiner*—Jeffrey Stucker
*Assistant Examiner*—Stephen Gucker
(74) *Attorney, Agent, or Firm*—Pierce Atwood LLP; Kevin M. Farrell; David J. Wilson (57) ABSTRACT

Provided herein are methods relating to inhibition of PUMA function for preventing or reducing myocardial cell death. A method for preventing or reducing ischemia/reperfusion induced myocardial cell death in a human is provided as are methods for identifying pharmaceuticals which interfere with PUMA function. Also herein provided is a method for reducing stem cell death in stem cell explants wherein the explants are intended to restore cardiac efficiency following cell death in response to coronary infarct.

2 Claims, 5 Drawing Sheets

METHODS FOR PREVENTING OR REDUCING ISCHEMIA/REPERFUSION INDUCED MYOCARDIAL CELL DEATH

RELATED APPLICATIONS

The present application is a Divisional of Non-Provisional application Ser. No. 11/103,851 filed on Apr. 12, 2005, which is a Non-Provisional of Provisional Application Ser. No. 60/561,640, filed on Apr. 13, 2004, the entire contents of which are incorporated by reference.

GOVERNMENT SUPPORT

This invention was made with Government support under NIH grant RO-1 HL68126 to P. Erhardt. The government has certain rights in the invention.

BACKGROUND OF THE INVENTION

The BH3-only Bcl-2 family protein PUMA (p53 upregulated modulator of apoptosis; also referred to as Bbc-3: Bcl-2 binding component-3) can bind the antiapoptotic Bcl-2 protein and facilitate the expression, conformational change, and mitochondrial translocation of Bax leading to apoptosis. PUMA has been reported to transmit p53-dependent apoptotic signals induced by DNA damage, hypoxia, or oncogenes. In addition, cytokine withdrawal, glucocorticoids, kinase inhibitors, and phorbol esters have also been shown to cause apoptosis through PUMA expression without involving p53. Recently, p73 emerged as another transcription factor eliciting apoptosis by PUMA-mediated Bax mitochondrial translocation.

Figure 1:
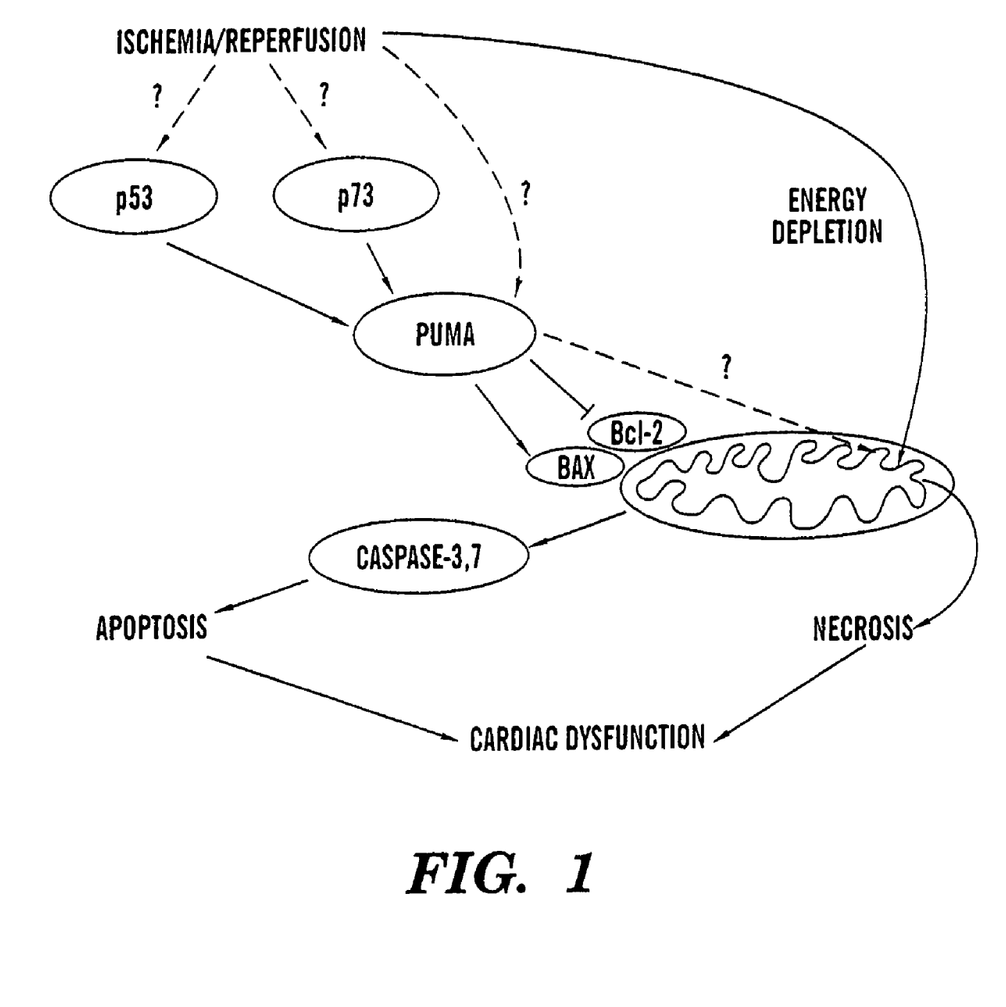
FIG. 1 is a diagrammatic representation of a molecular model for PUMA regulation and action in cardiomyocytes. PUMA is expressed in response to various stimuli through p53, p73, and other, yet unknown transcription factors and seems to act upstream of Bax. Endogenous PUMA mediates cardiomyocyte death in response to ischemia/reperfusion.

Cell death in the form of necrosis as well as apoptosis mainly accounts for cardiac contractile dysfunction upon ischemia/reperfusion. Although p53 overexpression can induce cell death in most cell types, the role of endogenous p53 in postischemic cardiac myocyte death remains controversial. On the other hand, Bax-ablation as well as cardiac Bcl-2 or Bcl-xL overexpression has been demonstrated to moderately improve tolerance to ischemia/reperfusion injury. Since PUMA is expressed in response to various stimuli through p53, p73, and other, yet unknown transcription factors and seems to act upstream of Bax, endogenous PUMA activation may significantly contribute to ischemia/reperfusion-induced cardiomyocyte death (FIG. 1).

SUMMARY OF THE INVENTION

In one aspect the present invention relates to a method for preventing or reducing ischemia/reperfusion induced myocardial cell death in a human. In this method, a composition effective to inhibit PUMA function in cardiomyocytes is administered to a human in need of such treatment. The composition may be any composition and may include a peptide, RNA, protein, small molecule or other composition. The composition may target PUMA function directly by down-regulating PUMA expression or by inhibiting binding of PUMA to interacting proteins, including but not limited to Bcl-2 or Bcl-xL. Alternatively, the composition may inhibit the function of PUMA by inhibiting the mitochondrial translocation of Bax. The composition of the invention may further inhibit some other, as yet unknown, function of PUMA. The composition is not required to be delivered in any specific manner, and may be delivered in conjunction with other therapies. Non-limiting examples of means for delivery include systemic or local administration. Methods of gene therapy may also be used in conjunction with the present invention wherein the composition to be administered to a human is a protein, peptide, or RNA.

The timing and duration of therapy is dependent upon clinical diagnosis. The composition effective to inhibit PUMA function may be administered during or subsequent to an ischemic attack to prevent any further ischemia/reperfusion induced myocardial cell death. In this instance, short therapies may be preferred as the effects of PUMA on cardiomyocyte death are likely to be immediate following an ischemic attack. Alternatively, the composition may be administered in the absence of such an ischemic event to an individual at risk for an ischemic attack, and in this instance, longer therapies may be preferred.

In a second aspect, the invention is directed to a method for identifying a drug which inhibits PUMA expression. In this method PUMA expressing cells in culture are contacted with a candidate drug to be tested for its ability to inhibit PUMA expression. The candidate drug may include a small molecule, peptide, RNA, or protein. The candidate drug may be added directly to the culture media or in the case that the candidate drug is a peptide, RNA, or protein, the PUMA-expressing cells may alternatively coexpress the candidate drug. The PUMA-expressing cells contacted with the candidate drug in culture are then assayed for PUMA expression such as by antibody or RNA in situ analysis. The PUMA expression levels in the cells contacted with the candidate drug are then related to levels of PUMA expression in matched cells that have not been contacted with the candidate drug. A candidate drug is identified as a drug based on its ability to inhibit PUMA expression to a significant degree.

In a third aspect, the invention is directed to a method for identifying a drug which substantially inhibits the activities of PUMA. In this method, PUMA may be expressed at endogenous levels, but the drug may hinder its function in modulating apoptosis. PUMA is known to bind Bcl-2 and Bcl-xL, and methods for identifying a drug which substantially inhibits the binding of PUMA to either Bcl-2 or Bcl-xL are within the scope of the present invention.

In a fourth aspect, the invention is directed to a method for identifying a drug which substantially inhibits the binding of PUMA to Bcl-2. In this method, PUMA protein is incubated with a Bcl-2 protein, or relevant binding domain thereof, and a candidate drug to be tested for its ability to interfere with the binding of PUMA to Bcl-2, under conditions appropriate for binding of PUMA to Bcl-2. The extent of binding is then determined and compared to PUMA/Bcl-2 binding in an otherwise identical incubation in which no candidate drug is included. A determination of inhibition of binding is made as the assessment of a substantial decrease in binding when the drug is employed in the assay as opposed to an evenly matched assay wherein the drug is not employed. A candidate drug is identified as a drug based on its ability to inhibit the binding of PUMA to Bcl-2 to a significant degree. Biochemical and/or cell culture assays may be utilized in this method.

In a fifth aspect, the invention is directed to a method for identifying a drug which substantially inhibits the binding of PUMA to Bcl-xL. In this method, PUMA protein is incubated with a Bcl-xL protein, or relevant binding domain thereof, and a candidate drug to be tested for its ability to interfere with the binding of PUMA to Bcl-xL, under conditions appropriate for binding of PUMA to Bcl-xL. The extent of binding is then determined and compared to PUMA/Bcl-xL binding in an otherwise identical incubation in which no candidate drug is included. A determination of inhibition of binding is made as the assessment of a substantial decrease in binding when the drug is employed in the assay as opposed to an evenly matched assay wherein the drug is not employed. A candidate drug is identified as a drug based on its ability to inhibit the binding of PUMA to Bcl-xL to a significant degree. Biochemical and/or cell culture assays may be utilized in this method.

In a sixth aspect, the present invention is directed to a method for reducing stem cell death in stem cell explants wherein the explants are intended to restore cardiac efficiency following cell death in response to coronary infarct. In this method, stem cells are contacted with a composition effective to inhibit PUMA function prior to introduction of the stem cells in a host. The resulting PUMA-deficient stem cells are then implanted into infarcted tissue rendering the developing cardiomyocytes more resistant to subsequent hypoxia/reoxygenation challenges. The composition of this method may be any composition, including a peptide, RNA, protein, or small molecule and/or combination thereof. The composition may target PUMA function directly by downregulating PUMA expression or by inhibiting binding of PUMA to interacting proteins, including but not limited to Bcl-2 or Bcl-xL. The composition may alternatively target PUMA function indirectly by inhibiting the mitochondrial translocation of Bax. The composition of this method may be any composition, including a peptide, RNA, protein, or small molecule and/or combination thereof.

BRIEF DESCRIPTION OF THE DRAWINGS

FIG. 2 illustrates that similar heart weights (A) and perfusion flow rates (B) were observed in the various study groups.

FIG. 3 illustrates the myocardial functional recovery after 20-min ischemia in the different study groups. Postischemic recovery of left ventricular developed pressure (A), +dP/dt$_{max}$ (B), and −dP/dt$_{min}$ (C) is expressed as the percentage of baseline preischemic values after 30, 60, 90, and 120-min reperfusion. Left ventricular end-diastolic pressure (D) is expressed in mmHg before ischemia and after 30, 60, 90, and 120-min reperfusion. *Significant difference of PUMA−/− values from the corresponding wild-type and PUMA heterozygous values ($p<0.05$).

FIG. 4 depicts infarct size (A) and lactate dehydrogenase release (B) in the various study groups. Infarct size was measured by triphenil tetrazolium cholride staining of hearts slices and expressed as the percentage of total myocardial area. LDH release was detected by a colorimetric assay from the coronary effluent and expressed as fold increase above baseline, and also normalized to heart weight. *Significant difference of PUMA−/− values from the corresponding wild-type and PUMA heterozygous values ($p<0.05$).

DETAILED DESCRIPTION OF THE INVENTION

The present invention is based on the finding that PUMA is a principle mediator of cardiomyocyte death in response to ischemia/reperfusion. More specifically, the present invention is based on the finding that loss of PUMA function results in improved tolerance to cardiac ischemia/reperfusion in mice. Disclosed herein is the observation that hearts of PUMA-deficient mice show significantly better functional recovery at the end of reperfusion than hearts from wild-type littermates, including recovery of left ventricular developed pressure (LVDP), first derivatives of left ventricular pressure (dP/dt), and left ventricular end-diastolic pressure (LVEDP). In addition, the functional recovery of PUMA-deficient hearts accompany corresponding inhibition of apoptosis and necrosis as well as reduced infarct size. Prior to the present invention, the role of PUMA in ischemia/reperfusion injury was unknown, as well as the superior therapeutic result of PUMA deficiency on postischemic functional recovery. The postischemic functional recovery resulting from loss of PUMA function, as disclosed herein, is far superior to that of Bax-deficiency and Bcl-2 or Bcl-xL overexpression, which are known in the art.

The present invention relates, in one aspect, to a method for preventing or reducing ischemia/reperfusion induced myocardial cell death in a human. The method comprises administering to a human a composition effective to inhibit PUMA function in cardiomyocytes in the human. The composition of this method may be any composition, including a peptide, RNA, protein, or small molecule and/or combination thereof. The only requirement of the composition is that it be effective in inhibiting PUMA function in cardiomyocytes. The composition need not be delivered in any specific manner, and may be delivered in conjunction with other therapies. Non-limiting examples of means for delivery include systemic or local administration and include methods for gene therapy wherein the composition is a protein, peptide, or RNA. The composition may target PUMA function directly by downregulating PUMA expression or by inhibiting binding of PUMA to interacting proteins, including but not limited to Bcl-2 or Bcl-xL. Alternatively, the composition may inhibit the function of PUMA by inhibiting the mitochondrial translocation of Bax. While not wishing to be bound by theory, the composition of the present invention may further inhibit some other, as yet unknown, function of PUMA. The composition may be administered during or subsequent to an ischemic attack to prevent any further ischemia/reperfusion induced myocardial cell death. In this method, short therapies may be preferred as the effects of PUMA on cardiomyocyte death are likely to be immediate following an ischemic attack. Alternatively, the composition may be administered in the absence of such an ischemic event to an individual at risk for an ischemic attack. In this instance, longer therapies may be preferred.

In another aspect, the present invention relates to a method for identifying a drug which inhibits PUMA expression. In the context of the present invention, such a drug may be identified using any of a number of routine methods which are known in the art. One such routine method comprises providing PUMA-expressing cells in culture. In this assay, it is not a strict requirement that the PUMA-expressing cells be cardiomyocytes, but only that they express PUMA. In the context of the present invention, the term "PUMA expressing cells" is meant to include a PUMA reporter gene in which PUMA regulatory sequences linked to a reporter gene is used in lieu of PUMA expression. In this case, the reporter gene may be assayed for expression. The PUMA may be endogenous or may be exogenous to the cells. The PUMA-expressing cells are then contacted with a candidate drug to be tested for its ability to inhibit PUMA expression. The candidate drug may comprise a small molecule, peptide, RNA, or protein. Contact of the PUMA-expressing cells with the candidate drug may be achieved by adding the candidate drug directly to the culture media. In the case that the candidate drug is a peptide, RNA, or protein, the PUMA-expressing cells may alternatively coexpress the candidate drug. The peptide, RNA, or protein candidate drug may be constitutively expressed or may be controlled by an inducible promoter. The PUMA-expressing cells which have been contacted with the candidate drug in culture are then assayed for PUMA expression using any of the routine methods which are known in the art. Endogenous or exogenous PUMA levels may be detected with PUMA antibodies or RNA in situ analysis. If the PUMA is exogenous, it may be expressed as a protein fusion, so that PUMA levels may be detected indirectly by assaying levels of the fusion. The PUMA expression levels in the cells which have been contacted with the candidate drug are then related to levels of PUMA expression in matched cells which have not been contacted with the candidate drug. Matched cells are defined as cells of the identical cell type and cells cultured in the same conditions and for the same period of time as those cells which have been contacted with the candidate drug, except that the matched cells have not been contacted with and/or coexpress the candidate drug. Finally, a candidate drug is identified as a drug based on its ability to inhibit PUMA expression in this assay to a significant degree. It is within the skill of one in the art to provide variations of this method to arrive at the same result.

In another aspect, the present invention relates to a method for identifying a drug which substantially inhibits the activities of PUMA. In this method, PUMA may be expressed at endogenous levels, but the drug may hinder its function in modulating apoptosis. PUMA is known to bind Bcl-2 and Bcl-xL, and methods for identifying a drug which substantially inhibits the binding of PUMA to either Bcl-2 or Bcl-xL are within the scope of the present invention.

A method for identifying a drug which substantially inhibits the binding of PUMA to Bcl-2 comprises first providing a PUMA protein. The term "PUMA protein" is meant to encompass the PUMA domain which binds Bcl-2. The term "Bcl-2 protein" is meant to encompass the Bcl-2 domain which binds PUMA. As such, it is not a requirement that the entire length of the PUMA or Bcl-2 sequence be utilized. The PUMA protein is then incubated with a Bcl-2 protein or relevant binding domain thereof and a candidate drug to be tested for its ability to interfere with the binding of PUMA to Bcl-2. The incubation is carried out under conditions appropriate for binding of PUMA to Bcl-2 which are known in the art. The extent of binding is then determined and compared to PUMA/Bcl-2 binding in an otherwise identical incubation in which no candidate drug is included. A determination of inhibition of binding is made as the substantial decrease in binding when the drug is employed in the assay. Any of a number of routine methods which are known in the art for determining the extent of inhibition of binding of two partners may be appropriate for the method of the present invention. The method may be biochemical and non-limiting examples of the same include GST pull-down assays, two-hybrid analysis, and/or his-tag analysis. Alternatively, the method may be carried out in cell culture. In cell culture, the conformational state of Bax protein, which is known to be dependent on PUMA binding to Bcl-2, may be assayed for determining the extent of inhibition of PUMA binding to Bcl-2.

It is an object of the present invention to provide a method for identifying a drug which substantially inhibits the binding of PUMA to Bcl-xL. Bcl-xL is a second binding partner to PUMA which is known in the art. This method may be carried out in much of the same manner as the method described above for identifying a drug which substantially inhibits the binding of PUMA to Bcl-2, except that Bcl-xL protein is utilized in this method instead of Bcl-2. As with Bcl-2, the Bcl-xL protein domain which binds PUMA may be substituted for the entire protein length.

It is within the skill of one in the art to provide variations of the methods described above to arrive at the same result. As new activities of PUMA are understood, the methods disclosed herein may be modified for use in identifying a drug which inhibits any new activities of PUMA. In such cases, the methods disclosed herein may be used as a guide and routine modifications may be made. In all cases for identifying drugs which inhibit PUMA function, methods conducive to high throughput analysis are preferred. Drug design by structural analysis may be utilized in lieu of random screening for compounds which inhibit the binding of PUMA to interacting proteins including but not limited to either Bcl-2 or Bcl-xL. The designed drugs may then be screened using the methods described above for identifying a drug which substantially inhibits the binding of PUMA to the interacting protein.

It is a further object of the present invention to provide a method for reducing stem cell death in stem cell explants intended to restore cardiac efficiency following cell death in response to coronary infarct. The method comprises contacting the stem cells with a composition effective to inhibit PUMA function prior to introduction of the stem cells in a host. PUMA-deficient stem cells can be implanted into infarcted tissue rendering the developing cardiomyocytes more resistant to subsequent hypoxia/reoxygenation challenges. The composition of this method may be any composition, including a peptide, RNA, protein, or small molecule and/or combination thereof. The only requirement of the composition is that it be effective in inhibiting PUMA function in the stem cells. The composition may target PUMA function directly by downregulating PUMA expression or by inhibiting binding of PUMA to interacting proteins, including but not limited to Bcl-2 or Bcl-xL. Alternatively, the composition may inhibit the function of PUMA by inhibiting the mitochondrial translocation of Bax. While not wishing to be bound by theory, the composition of the present invention may further inhibit some other, as yet unknown, function of PUMA. The stem cells may express the composition wherein the composition is a peptide, RNA, or protein. In one embodiment, the composition may be an antisense RNA able to bind PUMA RNA and down-regulate PUMA expression in the stem cells. In another embodiment, the composition may be a peptide able to bind PUMA protein and inhibit its function.

EXEMPLIFICATION

Example I

PUMA Deficiency Improves Tolerance to Cardiac Ischemia/Reperfusion

PUMA-/- hearts showed significantly better functional recovery at the end of reperfusion than hearts from wild-type littermates: the left ventricular developed pressure (LVDP) recovered to 95±5% in PUMA-/- and 23±7% in PUMA+/+ hearts (p<0.01). The postischemic recovery of $dP/dt_{max}$ was 101±3% vs. 20±6% in knockout and wild-type hearts, respectively (p<0.01). The left ventricular end-diastolic pressure also proved to be significantly lower in knockout hearts (3.5±0.5 vs. 23.9±3.6 mmHg in PUMA+/+ hearts, p<0.01). Heterozygous mice, however, rather copied the response of PUMA+/+ than knockout animals, indicating that decreased level of PUMA expression is not sufficient to prevent cardiac dysfunction. Consistent with heart perfusion studies, the functional recovery of PUMA-deficient hearts is accompanied with corresponding inhibition of apoptosis and necrosis as well as reduced infarct size.

PUMA knockout hearts showed significantly better functional recovery at each time point of reperfusion than hearts from wild-type littermates. FIG. 3 demonstrates the postischemic recoveries of left ventricular developed pressure, $dP/dt_{max}$, $dP/dt_{min}$, and left ventricular end-diastolic pressure. Heterozygous mice responded to ischemia/reperfusion similarly to their wild-type littermates.

Figure 4A:
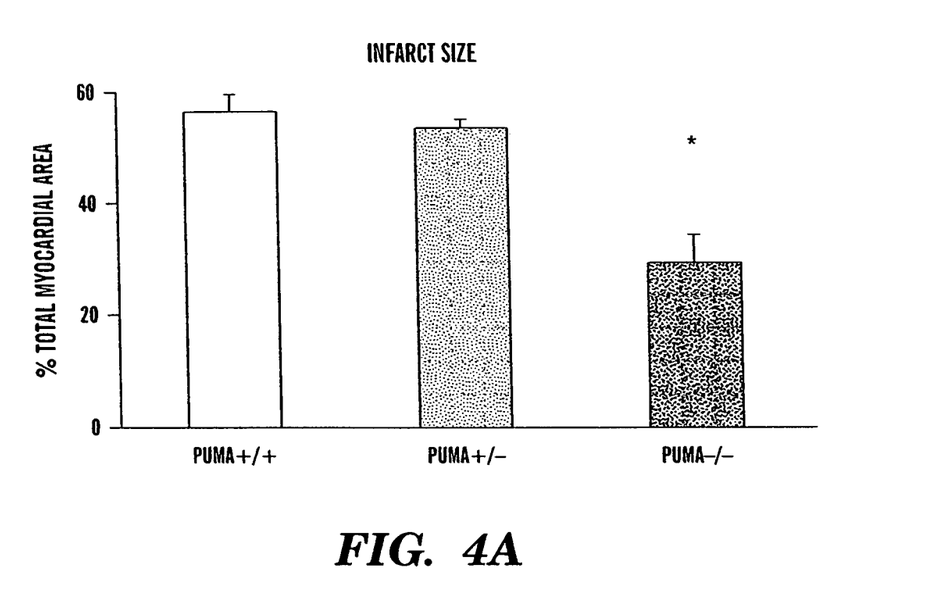
Figure 4B:
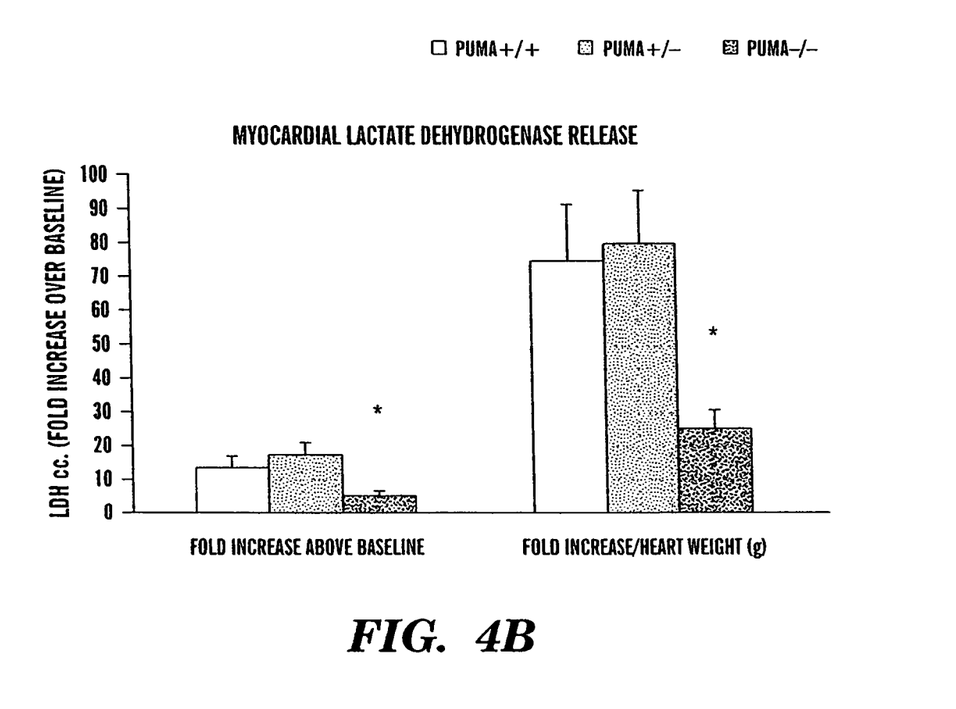

Consistent with the heart perfusion studies, triphenyl tetrazolium chloride staining revealed a significantly reduced infarct size in PUMA−/− hearts when compared to heterozygous and wild-type ones (FIG. 4A). Accordingly, lactate dehydrogenase release into the perfusate proved to be decreased in PUMA-deficient hearts related to heterozygous and wild-type experiments (FIG. 4B). A merely low level of apoptosis in the particular Langendorff model (1-2%) that appeared to be eliminated by targeted deletion of PUMA (data not shown).

METHODS OF THE INVENTION

Hearts from knockout (PUMA−/−), heterozygous (PUMA+/−), and wild-type (PUMA+/+) mice were perfused according to the Langendorff method and subjected to 20-min ischemia followed by 120-min reperfusion. Parameters of left ventricular function were monitored during the entire perfusion and hearts were processed for triphenyl tetrazolium chloride and TUNEL staining at the end of perfusion. Coronary effluent was collected to measure lactate dehydrogenase release.

Figure 2A:
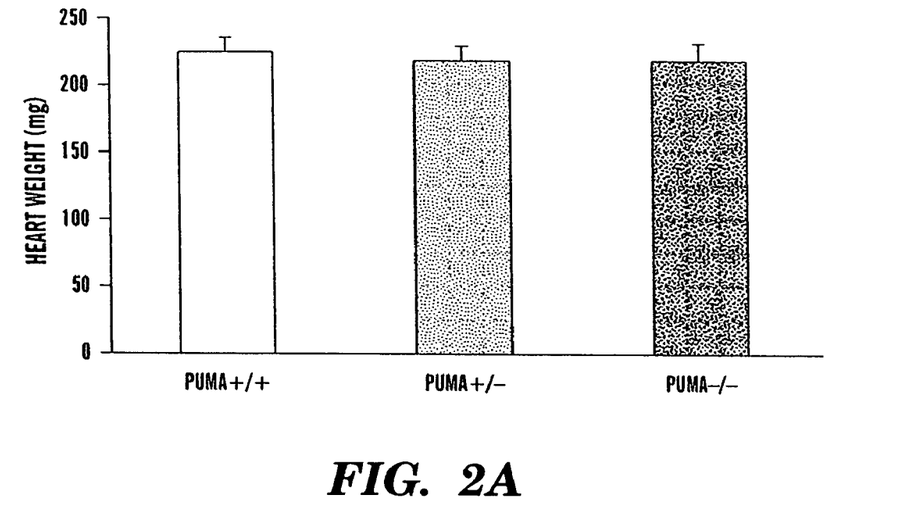
Figure 2B:
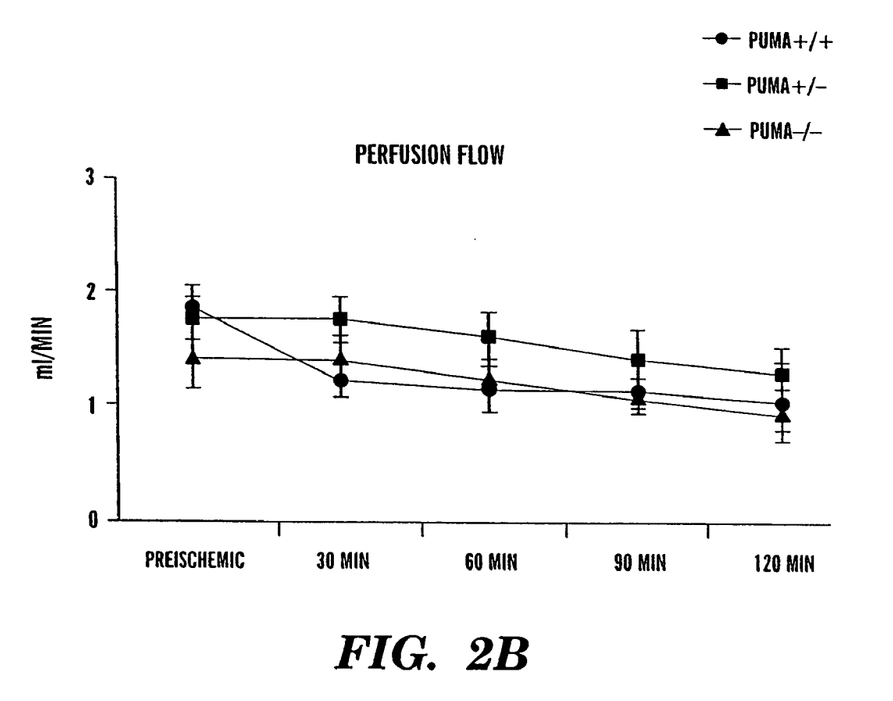
Figure 3A:
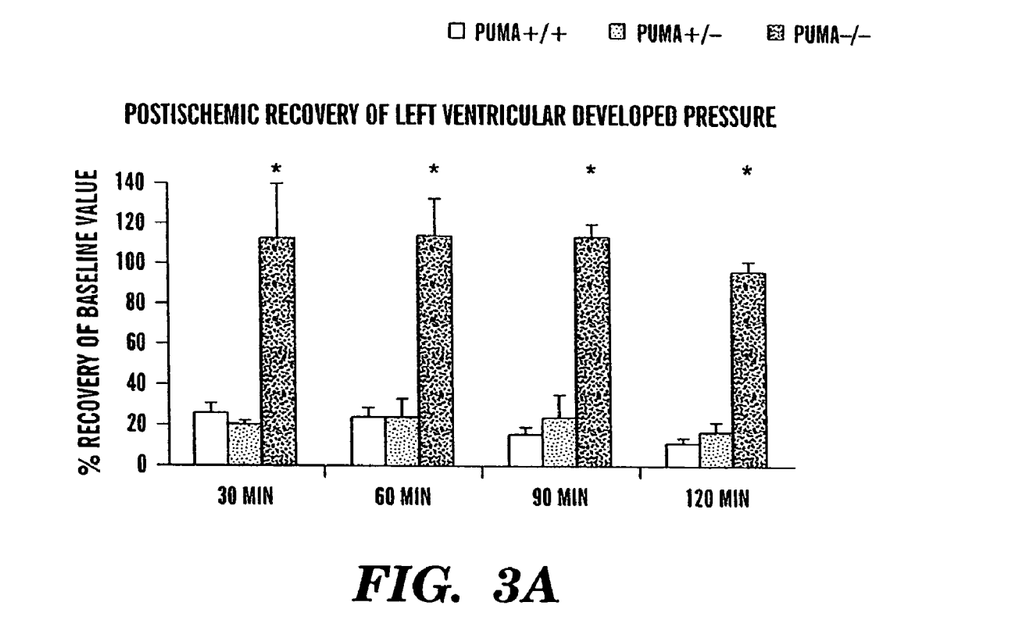
Figure 3B:
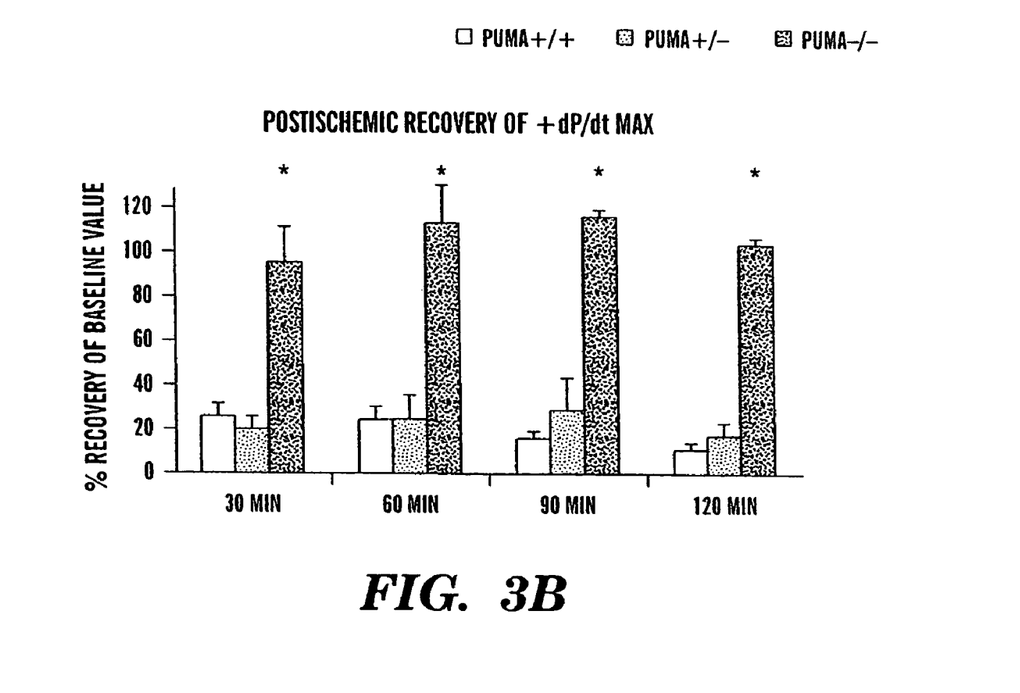
Figure 3C:
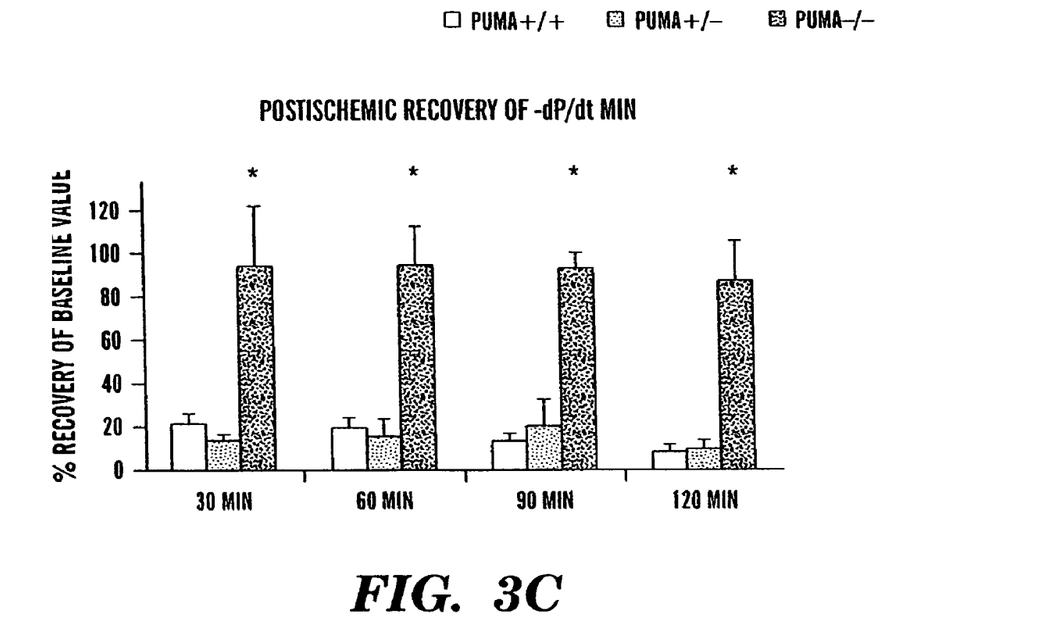
Figure 3D:
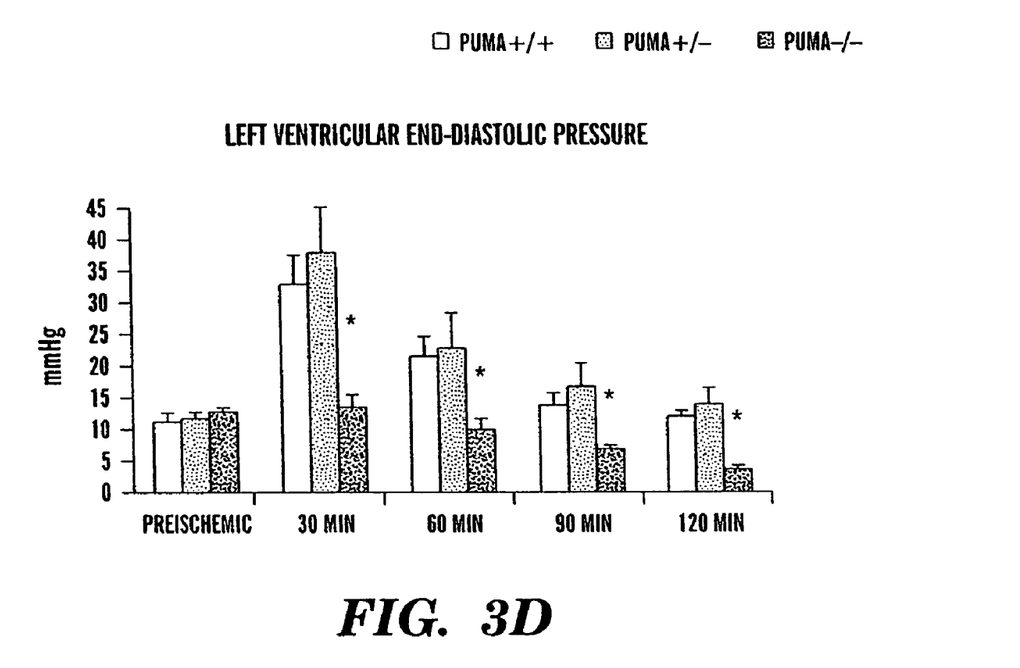

More specifically, PUMA knockout, heterozygous and wild-type mice weighing 20-30 g were anesthetized with pentobarbital (60 mg/kg i.p.), their chests were opened, and the hearts were rapidly excised and placed into ice-cold Krebs-Henseleit buffer. After trimming the atria and connective tissue, the aorta was cannulated with a blunted 20-gauge needle and the heart was attached to the Langendorff apparatus, then retrograde perfused at a constant pressure (80 mmHg) with a flow rate of 1-3 ml/min. The perfusion buffer was a modified phosphate-free Krebs-Henseleit buffer containing 118 mM NaCl, 4.7 mM KCl, 1.8 mM $CaCl_2$, 1.2 mM $MgSO_4$, 25 mM $NaHCO_3$, and 11 mM glucose. The perfusate was equilibrated at 37° C. with 95% $O_2$/5% $CO_2$ through a glass oxygenator to achieve pH 7.4. Hearts were exposed to a 20-min stabilization period then subjected to 20-min no-flow ischemia followed by 120-min reperfusion. Hearts were paced at 7 Hz through platinum wires placed on the epicardial surface of the right ventricle, however, the pacer was turned off during ischemia and turned on again in the fifth minute of reperfusion. During the entire perfusion period hearts were submerged into perfusion buffer at 37° C. A small custom-made polyvinyl chloride balloon was inserted into the left ventricle through the mitral valve and filled to achieve an end-diastolic pressure of 8-12 mmHg. All measurements were performed at the same balloon volume. Functional data of rat hearts (LVDP—left ventricular developed pressure, LVEDP—left ventricular end-diastolic pressure, $+dP/dt_{max}$, $-dP/dt_{min}$, and perfusion flow) were monitored during the entire perfusion using a commercially available data acquisition system (Powerlab, ADInstruments, Milford, Mass.). Recovery values of each parameter during reperfusion were compared to baseline functional performance in the individual hearts. At the end of each perfusion hearts were frozen for subsequent triphenyl tetrazolium chloride (TTC) staining, immunoblot analysis, and immunohistochemistry. Coronary effluent was collected during baseline perfusion and reperfusion to measure myocardial lactate dehydrogenase leakage. Heart weights and perfusion flow rates were similar in the different subgroups (FIG. 2).

The invention claimed is:

1. A method for identifying a drug which substantially inhibits the binding of PUMA to Bcl-2, the method comprising:
   a) providing a cardiomyocyte in vitro, said cardiomyocyte expressing PUMA and Bcl-2;
   b) providing a candidate drug to be tested for its ability to interfere with the binding of PUMA and Bcl-2;
   c) introducing said candidate drug to said cardiomyocyte;
   d) determining the extent of binding of PUMA and Bcl-2; and
   e) comparing the extent of binding determined in step d) to the extent of binding in an otherwise identical incubation in which no candidate drug is included, a substantial difference between the former and the latter indicating that the candidate drug is effective in substantially inhibiting the binding of PUMA to Bcl-2.

2. The method of claim 1, wherein the expression of PUMA and/or Bcl-2 is supplemented by the addition of an exogenous DNA construct, wherein said construct expresses PUMA and/or Bcl-2.

* * * * *

UNITED STATES PATENT AND TRADEMARK OFFICE
CERTIFICATE OF CORRECTION

PATENT NO. : 7,709,216 B2 Page 1 of 1
APPLICATION NO. : 11/891015
DATED : May 4, 2010
INVENTOR(S) : Peter Erhardt and Ambrus Toth It is certified that error appears in the above-identified patent and that said Letters Patent is hereby corrected as shown below:

Col. 8 lines 23-28 should read,
1. A method for identifying a drug which substantially inhibits the binding of PUMA to Bcl-2, the method comprising:
a) providing a cardiomyocyte in vitro, said cardiomyocyte expressing PUMA and Bcl-2;
b) providing a candidate drug to be tested for its ability to interfere with the binding of PUMA to Bcl-2;
c) introducing said candidate drug to said cardiomyocyte;
d) determining the extent of binding of PUMA to Bcl-2; and
e) comparing the extent of binding determined in step d) to the extent of binding in an otherwise identical incubation in which no candidate drug is included, a substantial difference between the former and the latter indicating that the candidate drug is effective in substantially inhibiting the binding of PUMA to Bcl-2.

Signed and Sealed this

Second Day of November, 2010

David J. Kappos
*Director of the United States Patent and Trademark Office*